(12) United States Patent
Kecman et al.

(10) Patent No.: US 8,636,741 B2
(45) Date of Patent: Jan. 28, 2014

(54) INTRAMEDULLARY ROD INSTRUMENT (75) Inventors: Maja Kecman, London (GB); Lisa Stroux, Heidelberg (DE); Alberto Verteramo, Leeds (GB); John Naybour, Leeds (GB)

(73) Assignee: Depuy International Limited (GB)

( * ) Notice: Subject to any disclaimer, the term of this patent is extended or adjusted under 35 U.S.C. 154(b) by 550 days.

(21) Appl. No.: 12/678,755

(22) PCT Filed: Sep. 19, 2008

(86) PCT No.: PCT/GB2008/003183
§ 371 (c)(1),
(2), (4) Date: Jul. 22, 2010

(87) PCT Pub. No.: WO2009/037471
PCT Pub. Date: Mar. 26, 2009

(65) Prior Publication Data
US 2010/0292694 A1    Nov. 18, 2010

(30) Foreign Application Priority Data

Sep. 21, 2007  (GB) .................................. 0718417.9

(51) Int. Cl.
*A61F 2/46*  (2006.01)
(52) U.S. Cl.
USPC .......................................... 606/86 R; 606/62
(58) Field of Classification Search
USPC .................................. 606/62–64, 86 R, 87, 88
See application file for complete search history.

(56) References Cited

U.S. PATENT DOCUMENTS

| 1,440,072 | A | 12/1922 | Greener |
| 4,453,539 | A | 6/1984 | Raftopoulos |
| 5,116,335 | A | 5/1992 | Hannon |
| 5,562,674 | A | 10/1996 | Stalcup |
| 5,628,749 | A | 5/1997 | Vendrely |
| 5,693,048 | A | 12/1997 | Stalcup |
| 5,830,216 | A | 11/1998 | Insall |
| 5,910,143 | A | 6/1999 | Cripe |
| 6,013,081 | A | 1/2000 | Burkinshaw |
| 6,193,723 | B1 * | 2/2001 | Cripe et al. ..................... 606/88 |
| 6,613,052 | B1 | 9/2003 | Kinnett |
| 7,794,467 | B2 | 9/2010 | McGinley |
| 8,287,541 | B2 * | 10/2012 | Nelson et al. .................. 606/63 |
| 2002/0198531 | A1 | 12/2002 | Millard |

(Continued)

FOREIGN PATENT DOCUMENTS

EP    687448 A1    12/1995
EP    689796 A1    1/1996

(Continued)

OTHER PUBLICATIONS

PCT International Search Report PCT/GB2008/003183 dated Apr. 8, 2009.

(Continued)

*Primary Examiner* — Ellen C Hammond (57) ABSTRACT

A femoral instrument for use in the intramedullary canal is described and includes an intramedullary rod having a tip at a free end. A body is attached to the intramedullary rod and has a face with a bone abutting portion. A centraliser mechanism is located within the rod and is operable to deploy and retract a plurality of members to engage and disengage an inner surface of the intramedullary canal.

16 Claims, 5 Drawing Sheets

(56) References Cited

U.S. PATENT DOCUMENTS

| | | |
|---|---|---|
| 2004/0153084 A1 | 8/2004 | Haney |
| 2006/0036248 A1 | 2/2006 | Ferrante |
| 2008/0097451 A1 | 4/2008 | Chen |
| 2009/0043310 A1 | 2/2009 | Rasmussen |
| 2009/0149964 A1 | 6/2009 | May |

FOREIGN PATENT DOCUMENTS

| | | |
|---|---|---|
| EP | 1444957 A1 | 8/2004 |
| EP | 1574177 A1 | 9/2005 |
| FR | 2943528 A1 | 10/2010 |
| WO | WO 9618351 A1 | 6/1996 |
| WO | WO 02058575 A1 | 8/2002 |
| WO | WO 2006090361 A2 | 8/2006 |
| WO | 2009006741 A1 | 1/2009 |
| WO | 2009037471 A2 | 3/2009 |

OTHER PUBLICATIONS

PCT Written Opinion PCT/GB2008/003183.
UK Search Report 0718417.9 dated Dec. 10, 2007.
Labourdette, P.; Femoral-Patellar Prosthesis and Ancillary Device for Making a Trochlear Impression for Receiving Said Prosthesis; European Publication No. EP687448A1; Dec. 20, 1995; English Abstract; MicroPatent Report; 2010 MicroPatent LLC.

* cited by examiner

INTRAMEDULLARY ROD INSTRUMENT

CROSS REFERENCE TO RELATED APPLICATION

This application is a National Stage 35 U.S.C. 371 of International Patent Application PCT/GB2008/003183 filed Sep. 19, 2008.

The present invention relates to a surgical instrument, and in particular to a surgical instrument including an intramedullary rod.

BACKGROUND OF THE INVENTION

Intramedullary rods can be used in knee arthroplasty procedures to provide a reference to which a cutting guide or block can be attached for performing a femoral cut. It will be appreciated that the present invention relates to intramedullary rods which provide a reference or some other feature or component which is used during preparation of the bone rather than to the type of rods which are placed inside the intramedullary canal to and secured with bone screws or similar as used to repair broken bones or in other trauma type applications.

Intramedullary rods typically are of order 40 cm or so long from the tip of the rod to the bone engaging formation which engages the bone surface in use. The end of the rods of such length become fixed in the intramedullary canal and so are self locating. However, the intramedullary canal varies from patient to patient in terms of its width, direction and straightness and so the intramedullary rod position can be compromised when using such long rods. Hence, the positioning of components attached to the rod, such as a cutting block, can also be compromised, and it can be difficult if at all possible to correctly position the cutting block.

It can be desirable to provide some angular adjustment so that the angular orientation of the cutting guide or block can be changed either to compensate for patient anatomy or otherwise to allow the femoral cut to be made at a preferred angle.

Figure 1:
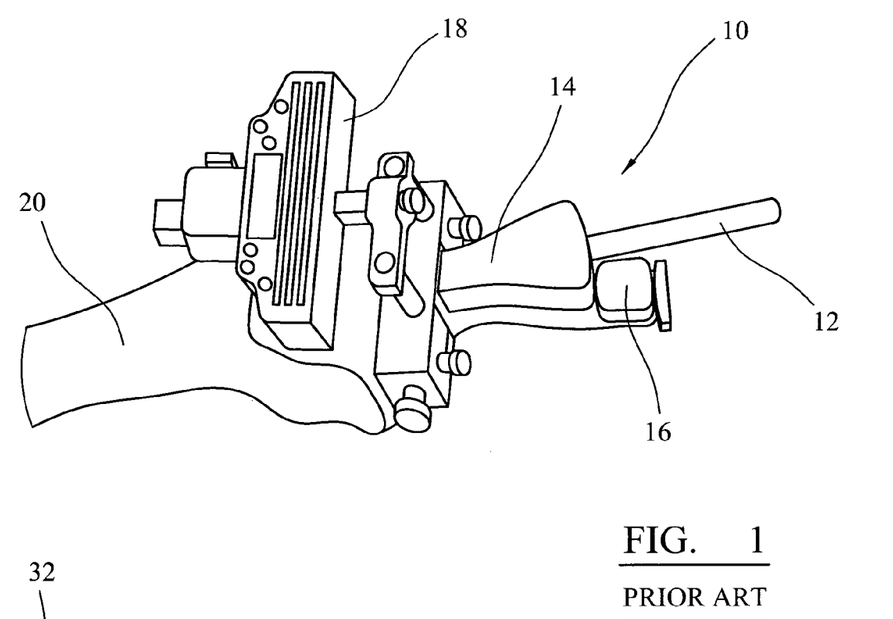
FIG. 1 shows a perspective view of a prior art femoral rod with angular adjustment.

Intramedullary rods which allow angular adjustment exist, but they can be difficult to use in practice. FIG. 1 shows an existing assembly 10 including an intramedullary rod 12 which is pivotably attached to a body by a pivot mechanism 14 which can be operated by a user to selectively change the angle of the rod, for example, by operating a lever 16 to engage/disengage teeth to allow the rod to freely pivot. Hence the angle of the rod 12 can be adjusted relative to a cutting block 18. However, such prior pivoting mechanisms can be difficult to use in practice. The lever to be operated is often small and difficult to operate with the rod 12 inserted into the femur 20. Also, because of the construction of the pivot mechanism, very little space can be available for the different selectable angles and so it can be hard to ensure that the correct angle is selected. Furthermore, there can be very little space available on which to display any scale so that the user can either see or check the angle that they want.

Therefore, it would be desirable to provide an intramedullary rod with angular adjustment which can be used more easily and/or which can be located in the intramedullary canal more easily.

BRIEF SUMMARY OF THE INVENTION

The present invention provides a femoral instrument including a short intramedullary rod with a centraliser mechanism so that the short rod can be self centralised in the intramedullary canal allowing the rod and other components attached to the rod to be more easily positioned relative to the bone in use.

The present invention also provides a femoral instrument including an intramedullary rod with an angular adjustment mechanism adapted to make the instrument easier to use in terms of its operation and reading of its scale.

According to a first aspect of the present invention, there is provided a femoral instrument, comprising: an intramedullary rod; a body to which the intramedullary rod is pivotably attached; and an angular adjustment mechanism, wherein the angular adjustment mechanism has a plurality of formations and is rotatable to present at least a one of the formations to abut a portion of the body to define the angle between the body and the intramedullary rod.

Preferably, the angular adjustment mechanism is rotatable about a longitudinal axis of the intramedullary rod.

The plurality of formations can be of various type and number. The plurality of formations can be recessed or can stand proud of a supporting surface. The formations can be individual elements or plural elements can make up a single formation. The formations can provide a surface or at least apart of a surface for abutable against a portion of the body. A formation or a plurality of formations can be provided on the body to interact with or co-operate with the formations of the angle adjustment mechanism.

The plurality of formations and the portion of the body can provide between them at least a first or a plurality of male members and/or at least a first or a plurality of female members and the male and female members can be adapted to engage, mate or otherwise co-operate with each other to define a plurality of different angles. Preferably, the plurality of formations and the portion of the body provide between them a rib and/or a plurality of slots in which the rib can engage. Each of the plurality of slots can be provided by a pair of recesses or notches. Preferably, the rib is provided on the body and the plurality of slots are provided on the angular adjustment mechanism.

The plurality of formations can provide at least two different angles and preferably at least three different angles, e.g., 3, 5 and 7 degrees, although a greater number of different angles can also be provided. The plurality of formations can provide a change in angle to both the left side and the right side of the instrument.

The angular adjustment mechanism can bare a plurality of indicia indicating the angular adjustment of the intramedullary rod. The indicia can be arranged on the adjustment mechanism so that an indicia indicating the angular adjustment corresponding to a current rotational position of the adjustment mechanism is presented to a user in normal use of the instrument, for example on an upper most surface of the angular adjustment mechanism.

The angular adjustment mechanism can be translatable along the longitudinal axis of the intramedullary rod to allow a different one of the plurality of formations to be selected.

The instrument can further include a biassing device which urges the angular adjustment mechanism toward the body to cause the at least one of the formations to abut the portion of the body.

The instrument can further include a handle. The angular adjustment mechanism can be translatable relative to the handle.

The instrument can further include a lock to lock the position of the angular adjustment mechanism.

The angular adjustment mechanism can include an element having a generally polygonal transverse cross section and being centrally mounted to be rotatable about the longitudinal axis of the rod. The element can have a plurality of generally flat faces. Each flat face can bare an indicia indicating an amount and/or a direction of angular adjustment. Preferably, the element, has a hexagonal, octagonal or decagonal cross section.

The instrument can further including a plurality of members deployable from within the Intramedullary rod to outside the intramedullary rod. The plurality of members can be effective to centralise the position of the Intramedullary rod within an intramedullary femoral canal when deployed. Preferably at least three members are provided. The members can be in the form of fins.

The instrument can further include a handle. The handle can include a button operable by a user to deploy the plurality of members. The button can be operable to drive a shaft or member extending at least partially along the interior of the intramedullary rod and linked to the members.

The length of the intramedullary rod from a bone engaging face of the body to a tip of the intramedullary rod can be less than 30 cm. The length of the intramedullary rod can be not more than 25 cm and more preferably not more than 20 cm. The length of the intramedullary rod can be between approximately 10 cm and 25 cm, more preferably between approximately 15 cm and 20 cm, and most preferably between approximately 15 and 18 cm. It has been found that making the rod too short prevents it from centralising in the intramedullary canal as the inner diameter of the canal is too great and that making the rod too long prevents the rod from becoming self-centralising as the plurality of members cannot act to locate the rod in the centre of the canal as movement of the tip or distal end of the rod is too constrained by the local geometry of the intramedullary canal.

A further aspect of the invention provides a femoral instrument, comprising an intramedullary rod having a tip at a free end; a body to which the intramedullary rod is attached and having a face with a bone abutting portion; and a centraliser mechanism located within the rod, wherein the centraliser mechanism is operable to deploy and retract a plurality of members to engage and disengage an inner surface of an intramedullary canal, and wherein the length of the intramedullary rod from the tip to the face of the body is less than 30 cm, and preferably less than 20 cm.

The further aspect of the invention can include one or more of the preferred features of the first aspect of the invention mentioned above.

A yet further aspect of the invention provides a method of stabilising a surgical device relative to a bone using an instrument having an intramedullary rod extending from a body having a bone engaging surface and further comprising a centraliser mechanism, comprising: introducing the intramedullary rod into the intramedullary canal of a patient with the centraliser mechanism in a non-deployed state; and operating the instrument to deploy the centraliser mechanism so as to stabilise the position of the tip of the intramedullary rod within the intramedullary canal.

The length between a tip of the intramedullary rod and the bone engaging surface can be less than 30 cm, less than 20 cm or between approximately 15 cm and 18 cm.

BRIEF DESCRIPTION OF THE DRAWINGS

An embodiment of the invention will now be described, by way of example only, and with reference to the accompanying drawings, in which.

Similar items in different Figures share common reference numerals unless indicated otherwise.

DETAILED DESCRIPTION OF THE INVENTION

Figure 2:
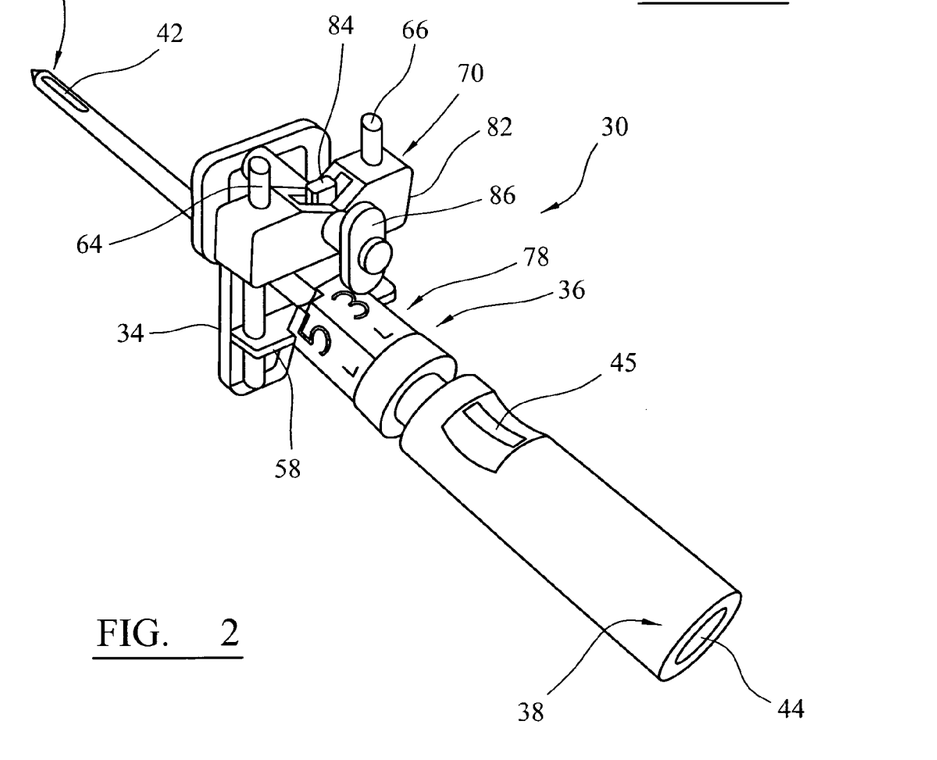
FIG. 2 shows a perspective view of a femoral instrument according to the invention.
Figure 3:
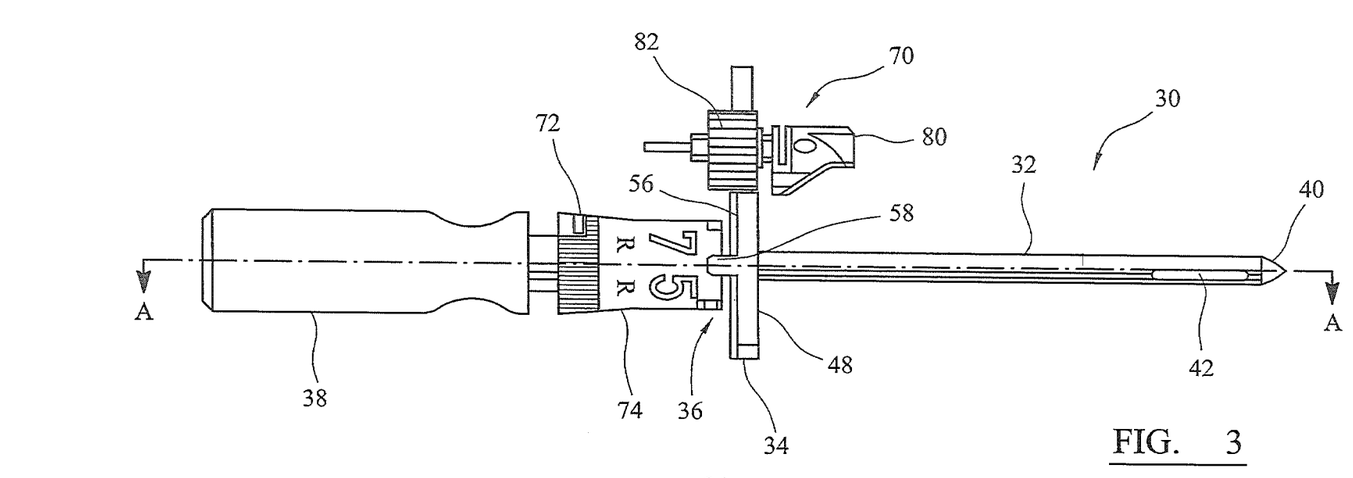
FIG. 3 shows a side view of the femoral instrument of FIG. 2.
Figure 4:
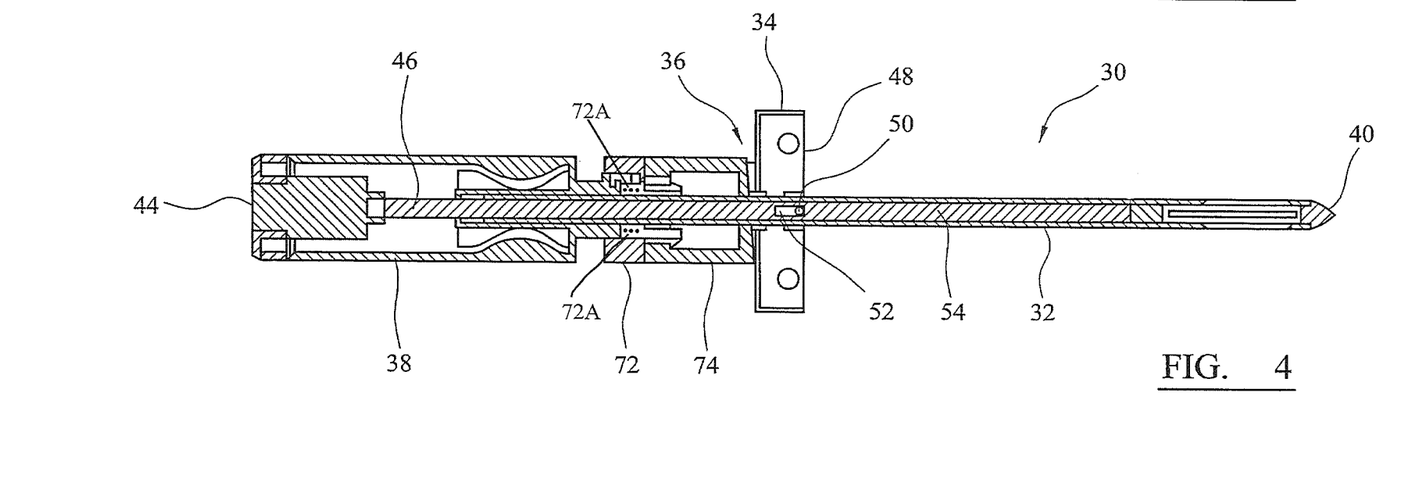
FIG. 4 shows a sectional view of the femoral instrument along line AA of FIG. 3.
Figure 5:
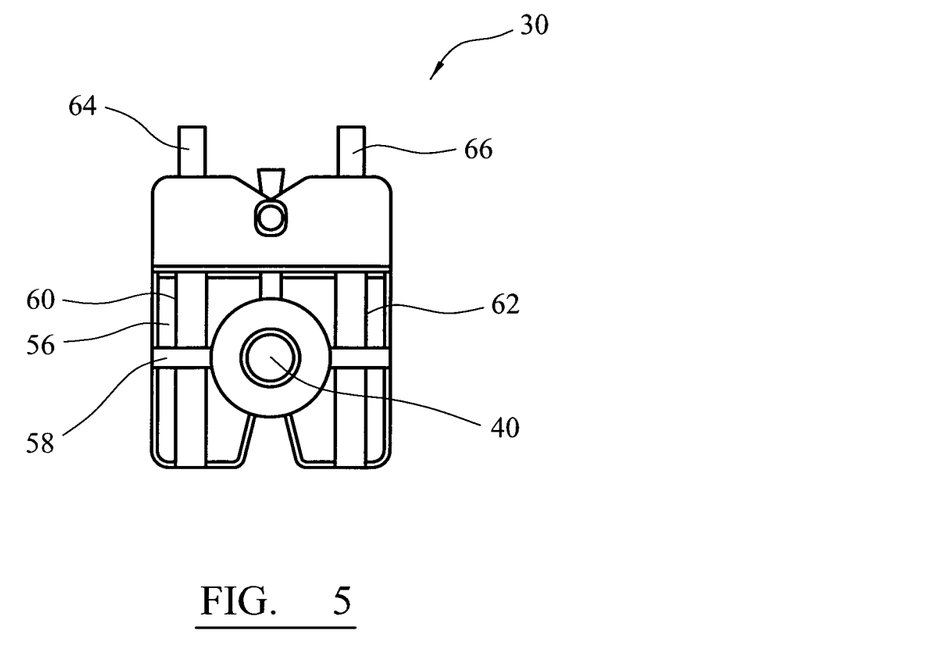
FIG. 5 shows a handle end view of the femoral instrument of FIG. 2.
Figure 6:
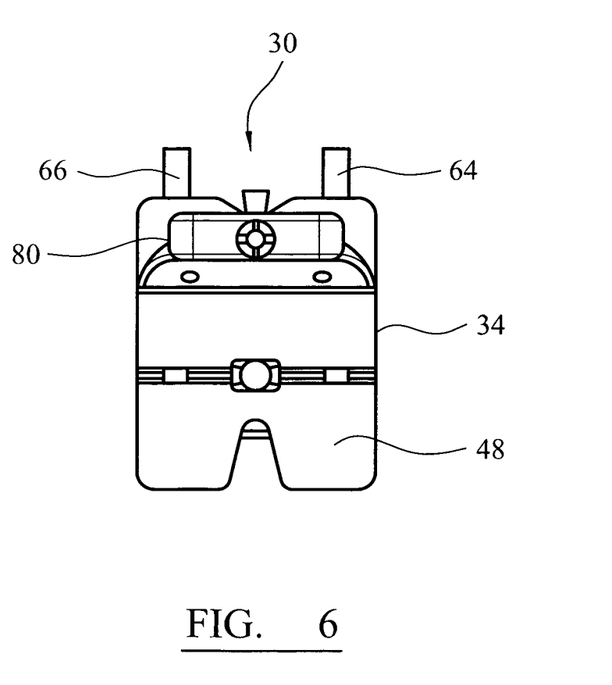
FIG. 6 shows a tip end view of the femoral instrument of FIG. 2.
Figure 7:
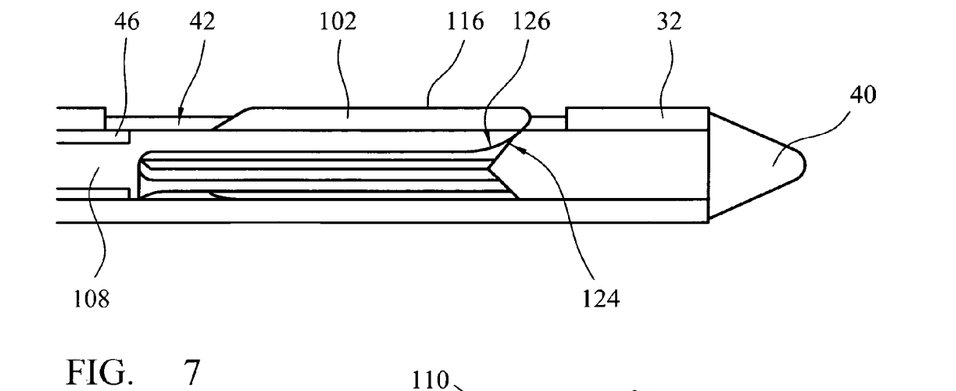
FIG. 7 shows a longitudinal cross sectional view through the tip of the instrument illustrating a part of a centraliser mechanism of the invention.
Figure 8:
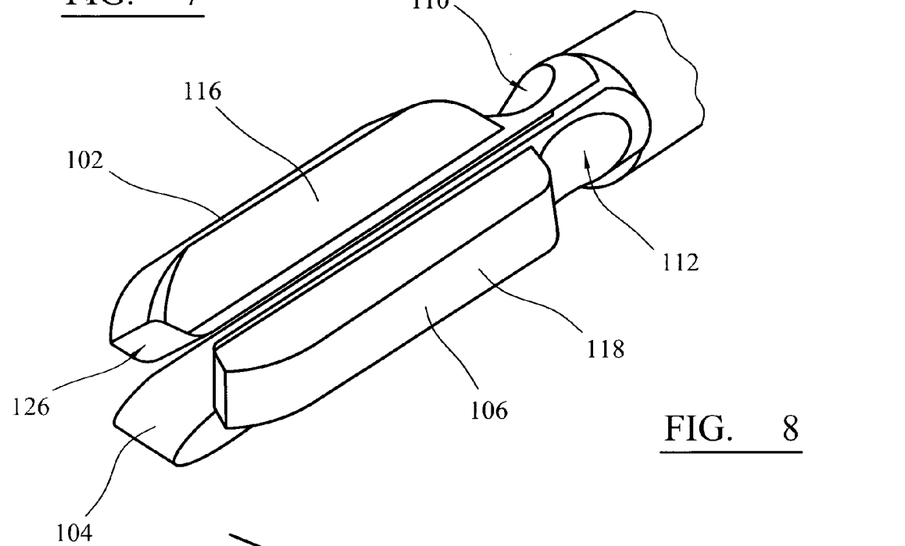
FIG. 8 shows a perspective view of a flares part of the centraliser mechanism shown in FIG. 7.
Figure 9:
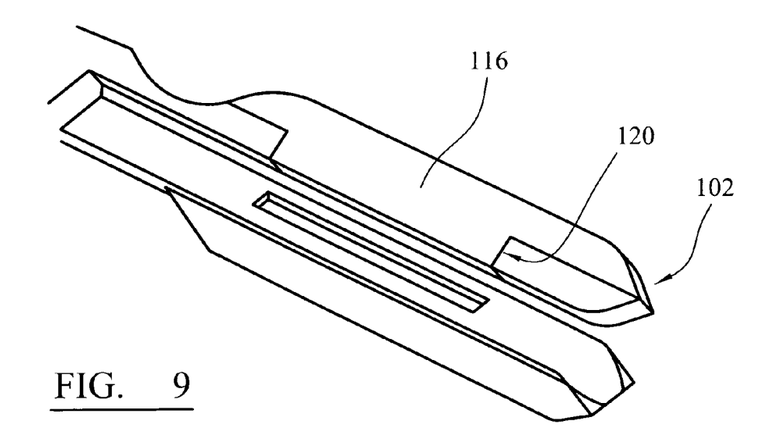
FIG. 9 shows a partial sectional view of the flares part shown in FIG. 8.
Figure 10:
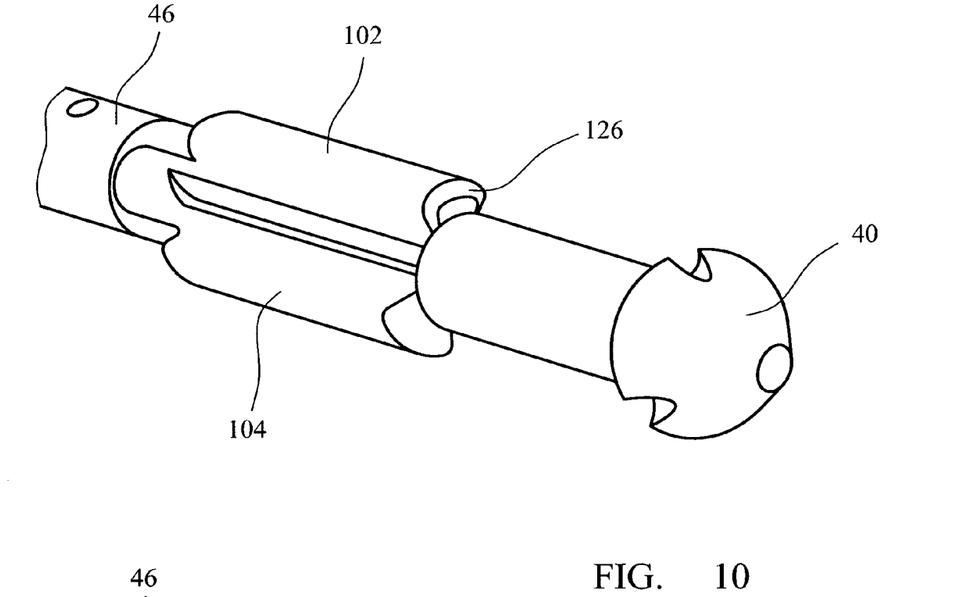
FIG. 10 shows a perspective view of the centraliser mechanism in a retracted state.
Figure 11:
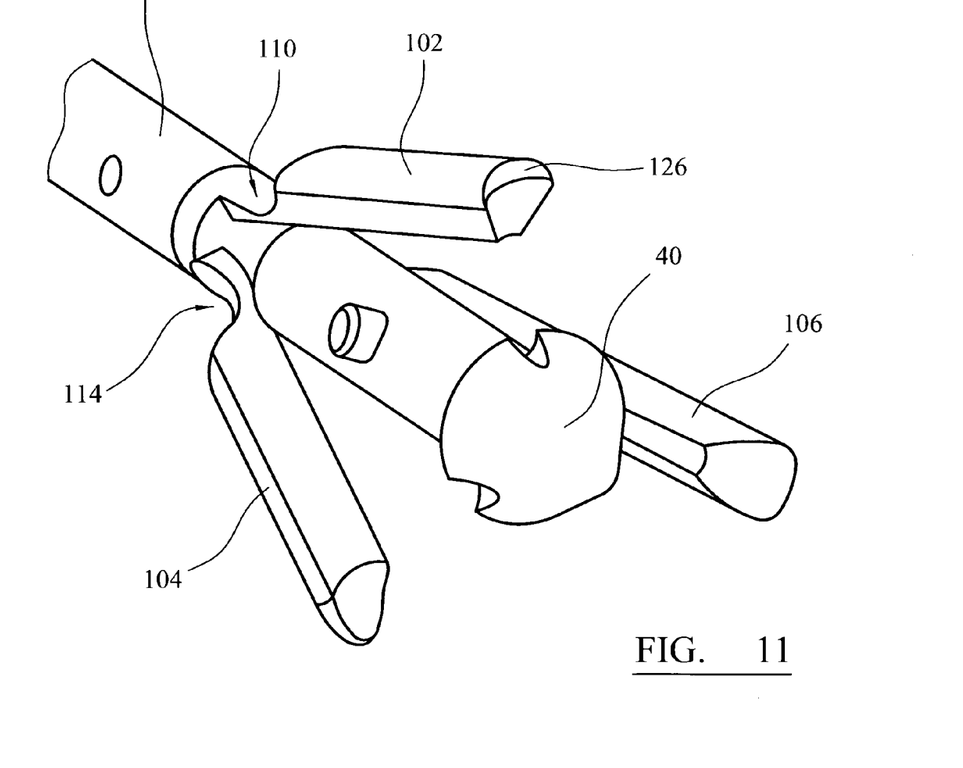
FIG. 11 shows a perspective view of the centraliser mechanism in a deployed state.

FIG. 2 shows a perspective view of an instrument 30 according to the present invention. FIG. 3 shows a side elevation of the instrument 30, FIG. 4 a cross-section through the instrument along line AA of FIG. 3, FIG. 5 an end view of the instrument from a handle end and FIG. 6 an end view of the instrument from a tip end. FIG. 7 shows a magnified cross sectional along line AA including the tip of the instrument illustrating a centraliser mechanism and FIGS. 8 and 9 are perspective views of parts of the centraliser mechanism. FIGS. 10 and 11 are perspective views illustrating the centraliser mechanism in use.

The instrument 30 includes an intramedullary (IM) rod 32, a body 34, an angular adjustment mechanism 36 and a handle 38.

The rod 32 has a generally tubular construction and includes a tip 40 at a free end thereof. Three apertures 42 are provided toward the free end of the rod. Within the rod three fin members 102, 104, 106 are provided which can be deployed from within the rod to exterior to the rod through respective apertures 42. The fin members can be deployed by operating a button 44 located in handle 38 to actuate a shaft or drive member 46 to slide within rod 32 to deploy the fins. The fins are attached by a linkage to shaft 46 so that when the shaft moves along the rod, the linkage causes the fins to be driven outwardly. The instrument also includes a fin retraction button 45 in an upper portion of the handle 38 operable by a user to retract the fins back within the rod. The fin retraction button 45 is connected to the shaft and when the retraction button 45 is actuated by a user, the shaft 46 moves back along the longitudinal axis of the rod, the linkage operates to draw the fins back within the rod and the rod returns the fin deployment button 44 back into an initial position from which the button 44 can be operated again to deploy the fins. Hence, the deploying and retracting the centralising and stabilising mechanism of the instrument is provided by an entirely mechanical mechanism. A spring (not shown) is provided as part of the instrument to urge the rod away from the tip 40 so that the fins 102, 104, 106 are normally in a non-deployed state. When button 44 is operated, the rod is driven against the biassing effect of the spring and a ratchet mechanism (not shown) interacts with the rod to hold the rod at a position along the longitudinal axis of the instrument. Button 45 interacts with the ratchet mechanism so that when button 45 is operated, the ratchet is released and the spring acts on the rod to drive the rod back toward the handle thereby withdrawing the fins. The operation of the fins members will be described in greater detail below with reference to FIGS. 7 to 11.

The body 34 has a generally plate-like construction and presents a flat femoral contact surface 48 toward the rod end of the instrument. The rod 32 is pivotably attached to the body 34 so as to allow relative pivoting between the body 34 and rod 32, as will be described in greater detail below. As illustrated particularly in FIG. 4, the pivot includes a pin 50 passing through a slot 52 in the drive member 46 so as to allow the drive member 46 to translate along the longitudinal axis of the rod while also allowing the rod 32 to pivot relative to body 34.

A rear face 56 of body 34 bears a rib 58 projecting away from body 34 and standing proud thereof. Rib 58 extends laterally across body 34 of the instrument. Rib 58 provides a part of the angular adjustment mechanism for the instrument as will be described in greater detail below.

Body 34 also includes first and second cylindrical formations 60, 62 accepting first and second pegs 64, 66 onto which a cutting guide and adjustment assembly 70 can be releasably attached.

Handle 38 is a generally hollow cylinder with upper and lower concave portions providing a grip for a user. The rod 32 terminates within the body of the handle which also includes button 44 and shaft 46 as described above. Handle 38 is attached to rod 32 to prevent relative rotation about the longitudinal axis of the rod. Between handle 38 and body 34, the angular adjustment mechanism 36 is provided.

The angular adjustment mechanism 36 further includes a first collar 72 and a second collar 74. The first collar 72 is mounted on an extension of the handle 38. The second collar 74 is mounted on an extension of the first collar 72 and extends around, and is centred on, the rod 32. The first and second collars are slidably mounted so as to the translatable along the longitudinal axis of the rod 32. A biasing spring 72A is provided in the second collar 72 to urge the first and second collars toward the body 34 in normal use. The first collar 72 is rotatable about the longitudinal axis of rod 32 in order to lock the second collar 74 in position.

The second collar 74 has a generally hexagonal cross-sectional shape. An end of collar 74 adjacent body 34 includes six notches, three pairs of which define three slots into which rib 58 can be accepted. Each notch of a pair of notches has a different depth, as particularly illustrated in FIGS. 3 and 4. Hence, when a pair of notches abuts against rib 58, the body 34 pivots relative to the longitudinal axis of rod 32 thereby changing the angular orientation between body 34 and rod 32.

The difference in depth between a pair of notches can be selected to provide the third changes in the angular orientation of the rod relative to the body away from the perpendicular. For example, in the illustrated embodiment, the depths of the notches are selected to provide 3, 5 or 7 degrees of angular variation. With a pair of notches in a first orientation, the relative angle can be changed in the right-hand or left-hand direction. By rotating the collar 74, it will be appreciated that the same pair of notches is provided, but rotated through 180 degrees, thereby providing the same magnitude of angular adjustment but in the opposite direction.

Flat outer surfaces of the collar 74 bear indicia 78 indicating the degree and direction of angular adjustment. The indicia are arranged on the collar 74 so that the degree and direction of angular adjustment with the collar in a current position is displayed on an uppermost surface of the instrument for ease of reading by the user. For example, as illustrated in FIG. 2, with the collar in the current position, a three degree to the left angular adjustment will be provided. It will be appreciated that in other embodiments, different magnitudes of angular adjustment can be provided and a grace number, or fewer number, of pairs of notches can be provided.

It will also be appreciated that combinations of formations other than the rib and slot arrangement described can be provided. For example, in other embodiments, a rib may be provided on collar 74 and slots provided on body 34. Also, it is not necessarily essential to use a rib and slots and any other combination of formations which allows non-parallel surfaces of the collar 74 and body 34 to abut to cause pivoting of the body, can be used. However, the slot and rib mechanism described herein has been found to be particularly usable in a surgical environment. Further, the collar 74 provides a large surface area on which the indicia can be displayed thereby facilitating ease of use of the instrument as the indicia are sufficiently large to be easily readable and are also locating in a position where they can be easily read by the user of the instrument while using the instrument.

A cutting guide assembly 70 is mounted on body 34. The cutting guide assembly 70 includes a cutting guide 80 having a slot therein for receiving a saw blade and a plurality of holes or other apertures for receiving drills and other cutting instruments as required, depending on the particular procedure being carried out. The cutting guide 80 is mounted on an adjustment component 82 including a threaded mechanism allowing the cutting guide 80 to be translated back and fourth in a direction generally perpendicular to the bone engaging phase 48 of body 34. A wheel 84 and lock 86 are also provided to allow the translational position of the cutting guide 80 to be adjusted and to lock the cutting guide in place.

As best illustrated in FIGS. 7 to 11, the centraliser mechanism includes three members or fins 102, 104, 106 arranged at approximately 120° intervals about the longitudinal axis of the instrument. The members are attached by a linkage mechanism to rod 46 which can be manually operated by button 44 to cause the members to be deployed. The three members are made from a single piece of flexible, preferably plastics, material 108 which has three portions of reduced thickness 110, 112, 114 which provides a mechanical hinge by which the individual members can bend away from their common core or body 108 by which they are attached to the rod 46.

Each member has an outer, bone engaging part 116, 118, 120 which is made of a harder or less flexible material than the core or body part of the members. This composite construction of the members allows the members to be flexed while still presenting a sufficiently robust bone engaging surface to allow the members to centralise the rod when they engage the inner surface of the intramedullary canal. As illustrated in FIG. 9, by the partial cross section through member 102, the outer part of the member 116 can include a projecting part in the form of a rib which can be push fit received in a corresponding mating slot 120 in the lower body part of the member 102. Suitable materials for the body part of the members are, for example, thermoplastics, ABS or PPSU. Suitable materials for the outer parts include, for example, polypropylene or polycarbonate.

The tip 40 has an inner end which has a sloped face 124, or faces which are presented to sloped, curved or chamfered free ends of the members, e.g. 126, so that the free ends of the members 102, 104, 106 will cam over the sloped face 124 of the tip and ride over the tip to deploy the members, when driven by the rod, as best illustrated in FIGS. 10 and 11. The outer casing of the instrument 32 can include three grooves in its outer surface extending along the longitudinal axis and positioned to receive and guide the bottom parts of the members as they are deployed. As described above, a ratchet mechanism holds the rod in position so that the members are retained in their deployed state illustrated in FIG. 11, until the ratchet is released by the user operating button 45, at which time the spring acting on the rod drives the rod back toward the handle part and the members return to their non-deployed state within the rod 32 as illustrated in FIGS. 10 (in which the rod is not shown) and 7.

The parts of the instrument can be made of suitable plastics materials and metals. Many of the components of the instrument can be made from biocompatible plastics, such as polypropylene, ABS, polyethylene and polyurethane and the rod 32, and any other preferably metal components, can be made from a suitable biocompatible metal, such as stainless steel.

Having described the instrument, use of the instrument in a knee arthroplasty procedure will now briefly be described.

Conventional IM rods are typically approximately 30 to 40 cm long and are introduced into the IM femoral canal to the level of the isthmus where the canal profile is at its narrowest and secures the IM rod in the proximal position. Various other components can then be assembled on the IM rod including a cutting block for performing the distal cut. Such rods are fluted to relieve IM pressure and permit the release of bone marrow in order to avoid embolisation. However, in some cases, the rod may not be able to extract enough bone marrow and part of it can still be pressed in the canal. This can cause migration of the bone marrow into blood vessel and consequent occlusion which leads to embolism. Hence, there are deficiencies in using long IM rods.

The instrument of the present invention has a relatively short IM rod. That is, the length of the IM rod between the bone engaging surface 48 and tip 40 is approximately 15 to 20 cm long. Hence, the tip 40 of the rod will not automatically be located in the narrowest part of the femoral canal and secured there. Instead, the fins can be deployed to provide a centraliser mechanism to centre the rod in the IM canal after it has been inserted, in order to avoid damaging the canal itself while the rod is introduced.

Hence, in use, the IM rod portion 32 is introduced into the IM canal of the femur until surface 48 of the body abuts against the condyles of the femur. When in position, the surgeon can operate button 44 to deploy the fins so as to centralise the rod within the IM canal and also stabilise the rod in position.

The cutting guide 80 is attached to body 34 and therefore the cutting guide 80 has the same angular orientation with respect to rod 32 as body 34. In order to adjust the angular orientation, the surgeon pulls the collar 74 toward handle 38 and then rotates the collar 74 until the desired angular adjustment is displayed on the uppermost surface. The collar is then released by the surgeon and the biasing spring 72A urges the collar 74 to engage the selected pair of notches with the rib 58 so that the body 34 pivots relative to the longitudinal axis of the rod 32.

If the surgeon wants to select a different size of angle or direction of angle, then the collar is again pulled towards the handle, rotated into the correct position and released to engage the rib again. When the appropriate angle and direction has been selected, then second collar 72 can be rotated to lock the adjustment mechanism in place. The cutting guard assembly 70 can then be adjusted to translate the cutting guide 80 to the desired height and the cutting guide 80 can then be pinned in place on the femur. The cutting guide 80 can then be released from the instrument by turning knob 86 to separate the instrument from the cutting guide 80 in one step and the instrument removed leaving the cutting block pinned in place. The remainder of the surgical procedure can be continued as usual.

It will be appreciated that the angular adjustment mechanism of the above described instrument is easy to use within a surgical environment as a large element is provided for adjusting and selecting the desired angular orientation. Further, any large surface areas provided on which the selected angle and direction can clearly be displayed and easily read during normal use of the instrument. Therefore, the present instrument provides the flexibility of angular adjustment of the IM rod without introducing any increased difficulty in reliable use of the instrument.

The invention claimed is:

1. A femoral instrument, comprising:
an intramedullary rod having a longitudinal axis;
a body to which the intramedullary rod is pivotably attached, the body having a proximal portion;
a first collar and a second collar disposed about the intramedullary rod, the second collar disposed between the first collar and the body, the second collar having a proximal and a distal end and a plurality of formations formed on the distal end of the second collar, the second collar being rotatable about the longitudinal axis to present at least one of the plurality of formations to abut the proximal portion of the body and thereby define a relative angle between the body and the intramedullary rod, wherein the first collar and the second collar are translatable along the longitudinal axis; and
a spring disposed between the body and the first collar to urge at least the second collar toward the body.

2. The femoral instrument of claim 1, wherein the intramedullary rod comprises a plurality of members deployable from within the intramedullary rod to engage and disengage an inner surface of an intramedullary canal.

3. The instrument of claim 1, further comprising a handle, and wherein the handle comprises a button operable to deploy the plurality of members.

4. The instrument of claim 3, wherein the handle further comprises a second button operable to retract the plurality of members.

5. The instrument of claim 1, wherein a tip of the rod includes a cam surface and each member has a sloping free end which can be driven against the cam surface to at least partially cause the member to be deployed.

6. The instrument of claim 1, wherein the length of the rod is between approximately 15 cm and 18 cm.

7. The instrument of claim 1, wherein each member includes a hinge part by which the member can be pivoted during deployment.

8. The instrument of claim 7, wherein each member is made from a first material and the material is shaped to provide the hinge part.

9. The instrument of claim 8, wherein each member includes an outer bone engaging part which is made from a second material, and wherein the second material is harder than the first material.

10. The instrument of claim 1, wherein the plurality of formations and the proximal portion of the body provide between them a rib and a plurality of slots, the plurality of slots being sized to accept the rib.

11. The instrument of claim 10, wherein the body comprises the rib and the distal end of the second collar has the plurality of slots.

12. The instrument of claim 1, wherein the second collar has an outer surface that has a plurality of indicia indicating the angular adjustment of the intramedullary rod.

13. The instrument of claim 1, further comprising a handle mounted to the first collar.

14. The instrument of claim 1, wherein the spring is disposed at least partially within the second collar.

15. The instrument of claim 1, wherein the spring urges the first collar and the second collar toward the body.

16. A method of stabilizing a surgical device relative to a bone comprising the steps of:

providing an instrument comprising an intramedullary rod extending from a body having a bone engaging surface, a first collar and a second collar disposed about the intramedullary rod, the second collar disposed between the first collar and the body, the second collar having a proximal and a distal end and a plurality of formations formed on the distal end of the second collar, the second collar being rotatable about the longitudinal axis to present at least one of the plurality of formations to abut the proximal portion of the body and thereby define a relative angle between the body and the intramedullary rod, and a spring disposed between the body and the first collar to urge at least the second collar toward the body;

introducing the intramedullary rod into the intramedullary canal of a patient; and translating the first collar and the second collar along the longitudinal axis in a direction away from the body;

rotating at least the second collar about the longitudinal axis to select a formation to provide an angle of orientation; and releasing the first and second collar, whereupon the biasing spring urges the second collar to abut against the body.

\* \* \* \* \*